US012728189B2

(12) United States Patent
Min

(10) Patent No.: US 12,728,189 B2
(45) Date of Patent: Sep. 8, 2026

(54) SYSTEMS AND METHODS FOR GENERATING AC VOLUME RECOMMENDATION FOR PLASMA COLLECTION

(71) Applicant: Fenwal, Inc., Lake Zurich, IL (US)

(72) Inventor: Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 517 days.

(21) Appl. No.: 18/262,604

(22) PCT Filed: Jan. 20, 2022

(86) PCT No.: PCT/US2022/013132
§ 371 (c)(1),
(2) Date: Jul. 24, 2023

(87) PCT Pub. No.: WO2022/159584
PCT Pub. Date: Jul. 28, 2022

(65) Prior Publication Data

US 2024/0082471 A1 Mar. 14, 2024

Related U.S. Application Data

(60) Provisional application No. 63/141,075, filed on Jan. 25, 2021.

(51) Int. Cl.
*A61M 1/34* (2006.01)
*A61M 1/36* (2006.01)

(52) U.S. Cl.
CPC .......... *A61M 1/3496* (2013.01); *A61M 1/361* (2014.02)

(58) Field of Classification Search
CPC .... A61M 1/385; A61M 1/3672; A61M 1/361; A61M 1/3496
See application file for complete search history.

(56) References Cited

U.S. PATENT DOCUMENTS 5,194,145 A 3/1993 Schoendorfer
5,360,542 A 11/1994 Williamson, IV
(Continued)

FOREIGN PATENT DOCUMENTS

WO 2019226654 A1 11/2019

OTHER PUBLICATIONS

European Search Report and Opinion Issued by the European Patent Office for Application No. 22743164.0, dated Nov. 18, 2024 (11 pages total).

*Primary Examiner* — Leslie R Deak
(74) *Attorney, Agent, or Firm* — Cook Alex Ltd.

(57) ABSTRACT

A method for determining a total volume of anticoagulant required for performing a plasmapheresis procedure prior to connecting the donor to the fluid flow circuit, by determining: a total blood volume for a donor, volume of plasma to be collected, a volume of anticoagulant that will be collected together with the plasma and estimating a separation efficiency for the blood separator. Then calculating volume of anticoagulant to be returned to the donor based on the separation efficiency, total volume of anticoagulant to be used and suggesting and attaching either a single container or multiple containers of anticoagulant based on said calculations. The system comprises a touch screen for receiving input and providing said calculation of a total volume of anticoagulant needed for the procedure, and recommendation the number of containers of anticoagulant needed.

21 Claims, 6 Drawing Sheets

(56) References Cited

U.S. PATENT DOCUMENTS

| | | | | |
|---|---|---|---|---|
| 8,840,790 | B2 | 9/2014 | Wegener | |
| 10,046,278 | B2 | 8/2018 | Kusters | |
| 11,386,993 | B2 | 7/2022 | Case | |
| 2013/0267884 | A1* | 10/2013 | Boggs | A61M 1/36225<br>604/6.02 |
| 2018/0344921 | A1* | 12/2018 | Ragusa | A61M 1/3644 |
| 2020/0147289 | A1 | 5/2020 | Patel | |
| 2021/0015989 | A1 | 1/2021 | Patel | |
| 2021/0353841 | A1* | 11/2021 | Patel | G01N 33/48 |

* cited by examiner

SYSTEMS AND METHODS FOR GENERATING AC VOLUME RECOMMENDATION FOR PLASMA COLLECTION

CROSS-REFERENCE TO RELATED APPLICATIONS

The present application is the U.S. National Stage Application of PCT Application No. PCT/US2022/013132, filed Jan. 20, 2022, which claims the benefit and priority to U.S. Provisional Patent Application Ser. No. 63/141,075, filed Jan. 25, 2021, the contents of which are hereby incorporated by reference.

BACKGROUND

The present application relates to systems and method for performing plasmapheresis and, more particularly, to plasmapheresis systems and methods in which an estimate of the total volume of anticoagulant required for the procedure is determined in advance based on donor-specific characteristics, and a container of anticoagulant having a volume sufficient for the entire procedure is connected to the system prior to the start of the procedure.

Plasmapheresis is an apheresis procedure in which whole blood is withdrawn from a donor, the plasma separated from the cellular blood components (red blood cells, platelets and leukocytes) and retained, and the cellular blood components returned to the donor. The separation of the plasma from the cellular components is typically accomplished in an automated procedure by centrifugation or membrane filtration.

In automated plasmapheresis, whole blood is drawn from the donor, mixed at a specified ratio with anticoagulant ("AC"), and then separated into anticoagulated plasma and red blood cells and other cellular components.

The volume of plasma that may be collected during a plasmapheresis procedure varies from donor to donor. Further, the volume of plasma that may be collected from any particular donor may be determined in a number of different ways based on various donor-specific characteristics.

Methods for determining the volume of raw plasma that may be withdrawn from any particular donor, consistent with donor safety and comfort, typically include an estimation/determination of the donor's total blood volume using donor-specific characteristics, and then determining the total volume of raw plasma that may be collected from that donor. See, e.g., WO 2019/226654 and U.S. Ser. No. 17/078,824, filed Oct. 23, 2020, both of which are incorporated by reference herein, and which disclose systems and methods for the optimization of plasma collection volumes based upon the use of donor-specific characteristics for determining a target collection volume of raw plasma for the donor.

As can be appreciated, the volume of anticoagulant that will be required for any particular plasmapheresis procedure will depend upon the amount of raw plasma that is to be collected. With this volume varying from donor to donor, it is desirable to ensure that a single container holding a volume anticoagulant sufficient for the entire collection procedure is connected to the system at the start. Otherwise, the operator may need to pause the procedure to replace the container of anticoagulant, leading to increased procedure time (which could result in increased donor discomfort or perhaps a donor reaction), as well as to greater expense due to using multiple containers of anticoagulant. By way of the present application, a method and system are provided that estimates the total amount of anticoagulant that will be required for the plasma collection procedure and alerts the operator in advance to obtain additional container(s) of anticoagulant so that they will be available to exchange with the original container of anticoagulant before or simultaneously with it running out, or, alternatively, facilitates the use of a single container of anticoagulant for the plasmapheresis procedure.

SUMMARY

The present application has several aspects. In a first aspect, a method is provided for performing plasmapheresis using a fluid flow circuit and a blood separator, comprising: determining a total blood volume (TBV) for a donor, determining a volume of plasma (VP) to be collected from the donor based on donor-specific characteristics; determining a volume of anticoagulant ($V_{ACP}$) that will be collected together with the volume of plasma VP; calculating a volume of anticoagulant to be returned to the donor ($V_{ACR}$) based on a separation efficiency for the blood separator, calculating a total volume of anticoagulant ($V_{ACT}$) to be used; and either i) preparing one or containers of anticoagulant for attachment to the fluid flow circuit containing at least $V_{ACT}$, or ii) attaching a single container of anticoagulant to the fluid flow circuit containing at least $V_{ACT}$; wherein the recited steps are performed prior to connecting the donor to the fluid flow circuit.

In a second aspect, the donor-specific characteristics comprise weight and hematocrit. The hematocrit may be a default value which is representative of a worst-case scenario, such as a hematocrit of 54%. Alternatively, the hematocrit may be the measured hematocrit of the donor.

In a third aspect, the donor-specific variables comprise weight, height, and hematocrit.

In a fourth aspect, the donor-specific variables comprise weight, height, gender, and hematocrit.

In a fifth aspect, the one or more containers or the single container contain 250 mL of anticoagulant, if VACT<250 mL; 500 ml of anticoagulant, if 250 mL<VACT<500 mL; 750 mL of anticoagulant, if 500 mL<VACT<750 mL; and 1000 mL of anticoagulant, if 750 mL<VACT<1000 mL.

In a sixth aspect, $V_{ACP}$=VP/(1+ACR*(1−Hct/100)); wherein ACR is the ratio of anticoagulant to whole blood and Hct is the hematocrit of the donor.

In a seventh aspect, the separation efficiency for the blood separator is based, at least in part, on a hematocrit of the donor.

In an eighth aspect, the separation efficiency for the blood separator is based, at least in part, on a ratio of anticoagulant to whole blood (ACR) to be used.

In a ninth aspect, $V_{ACT}=V_{ACP}+V_{ACR}$. Alternatively, $V_{ACT}$ may be based on the estimated volume of whole blood to be processed to reach the volume of plasma to be collected, which, in turn, is based on separation efficiency.

In a tenth aspect, $V_{ACT}$ additionally includes a volume of anticoagulant to be used for priming the fluid flow circuit and blood separator.

In an eleventh aspect, $V_{ACT}$ is increased to provide a margin of safety, such that $V_{ACT}$ is increased by from 25 mL to 50 mL.

In a twelfth aspect, an automated system for separating plasma from whole blood is provided comprising a disposable fluid flow circuit including a separator for separating whole blood into a plasma fraction and a concentrated cell fraction and a reusable hardware component comprising a programmable controller having a touch screen for receiving input from an operator and configured to provide, based on operator input, a calculation of a total volume of anticoagulant needed for the procedure.

In a thirteenth aspect, the programmable controller is configured to calculate: a total blood volume (TBV) for a donor; a volume of plasma (VP) to be collected from the donor based on donor-specific characteristics; a volume of anticoagulant ($V_{ACP}$) that will be collected together with the volume of plasma VP; a volume of anticoagulant to be returned to the donor ($V_{ACR}$) based on an estimated separation efficiency for the separator; a total volume of anticoagulant ($V_{ACT}$) to be used wherein $V_{ACT}=V_{ACP}+V_{ACR}$; and to display $V_{ACT}$ on the touch screen.

In a fourteenth aspect, the controller is further configured to make a recommendation as to a volume of a single container of anticoagulant to be attached to the disposable fluid flow circuit based on $V_{ACT}$, wherein the recommendation is that either a single container or multiple containers are provided that contain 250 mL of anticoagulant, if VACT<250 mL; 500 ml of anticoagulant, if 250 mL<VACT<500 mL; 750 mL of anticoagulant, if 500 mL<VACT<750 mL; and 1000 mL of anticoagulant, if 750 mL<VACT<1000 mL.

Other aspects will become apparent upon reference to the following description and accompanying drawings.

DETAILED DESCRIPTION

A more detailed description of the systems and methods in accordance with the present disclosure is set forth below. It should be understood that the description below of a specific device and method is intended to be exemplary, and not exhaustive of all possible variations or applications. Thus, the scope of the disclosure is not intended to be limiting, and should be understood to encompass variations or embodiments that would occur to persons of ordinary skill.

In the context of the present application, plasmapheresis is performed on an automated system comprising a hardware component, generally designated 10, and a disposable set, generally designated 12, to collect plasma. With reference to FIGS. 1-5, and as described in greater detail below, the disposable set 12 consists of an integrally connected separator, containers, and tubing to transport blood and solutions within a sterile fluid pathway.

Figure 1:
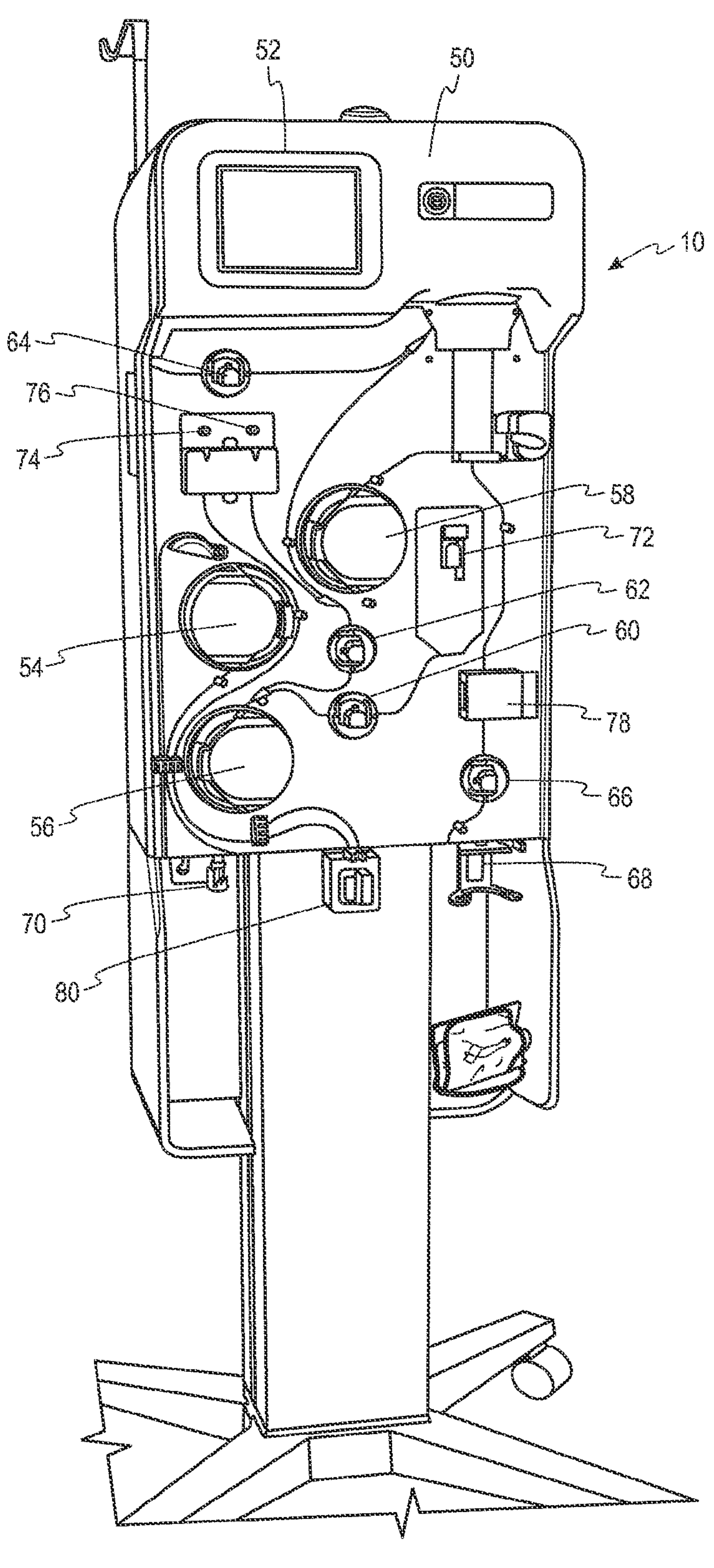
FIG. 1 is a perspective view of an exemplary plasmapheresis instrument suitable for use in the system and method of the present application.
Figure 2:
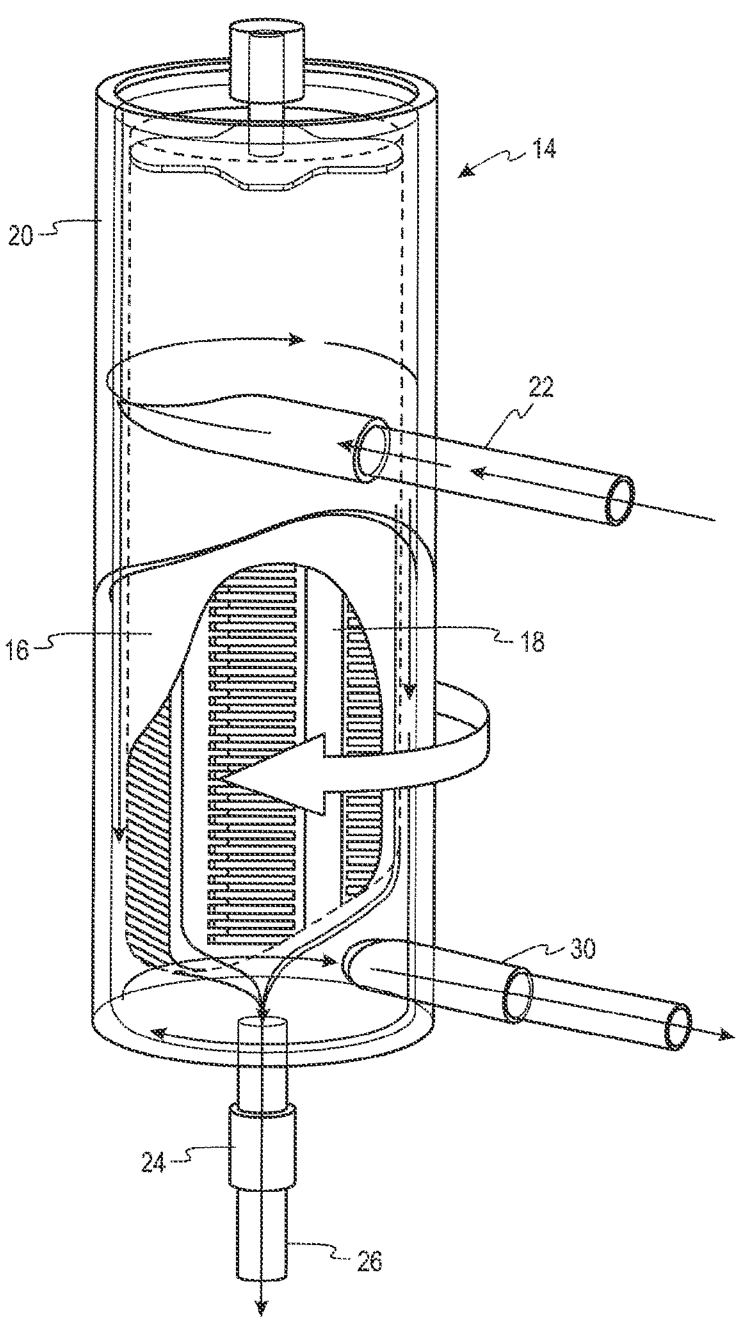
FIG. 2 is a perspective view of a spinning membrane separator of the type incorporated in a disposable set, with portions broken away to show detail, usable with the plasmapheresis system of FIG. 1.
Figure 3:
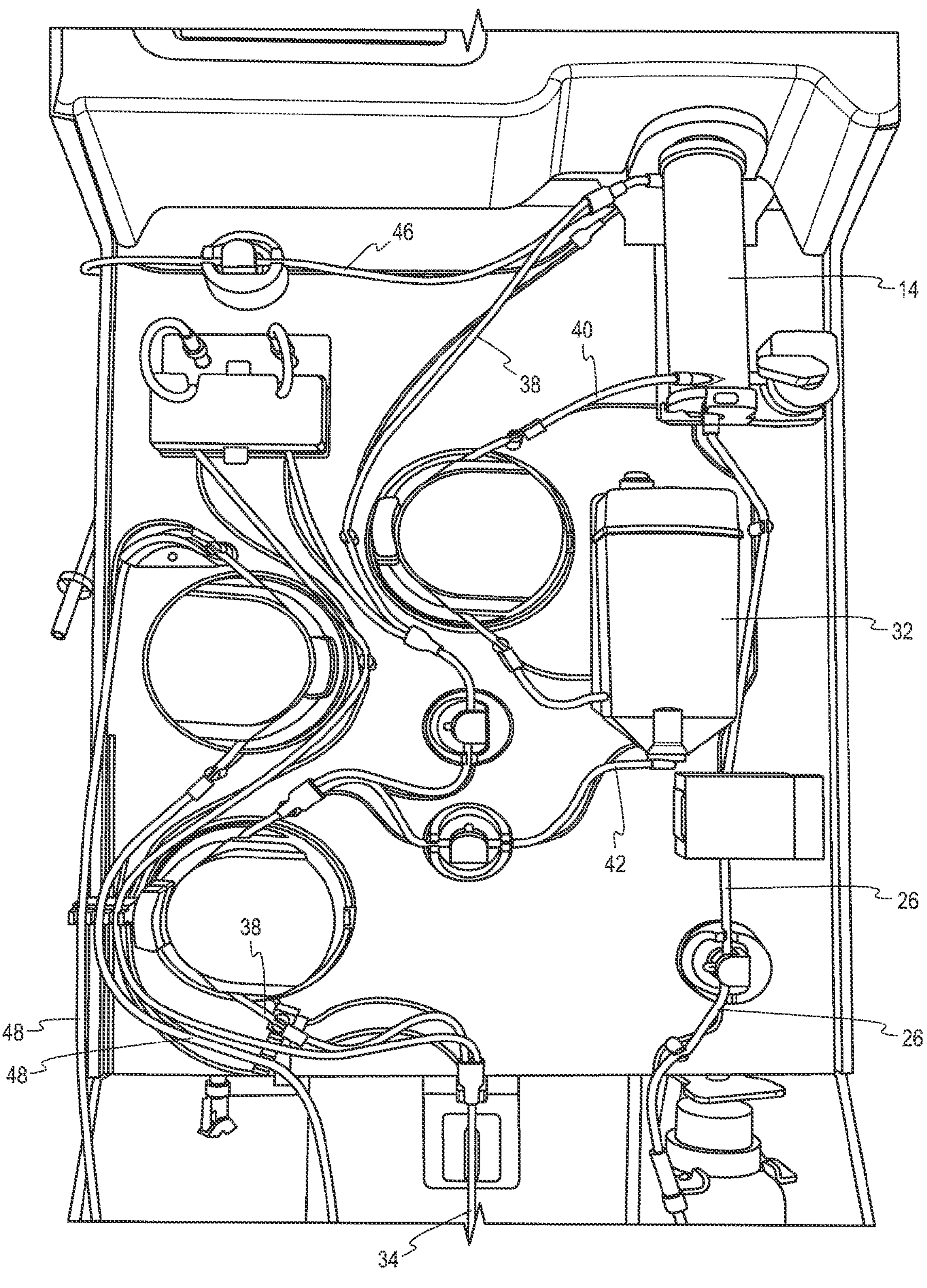
FIG. 3 is a perspective view of the front panel of the plasmapheresis system of FIG. 1 showing the components of the disposable set that are mounted thereto.
Figure 4:
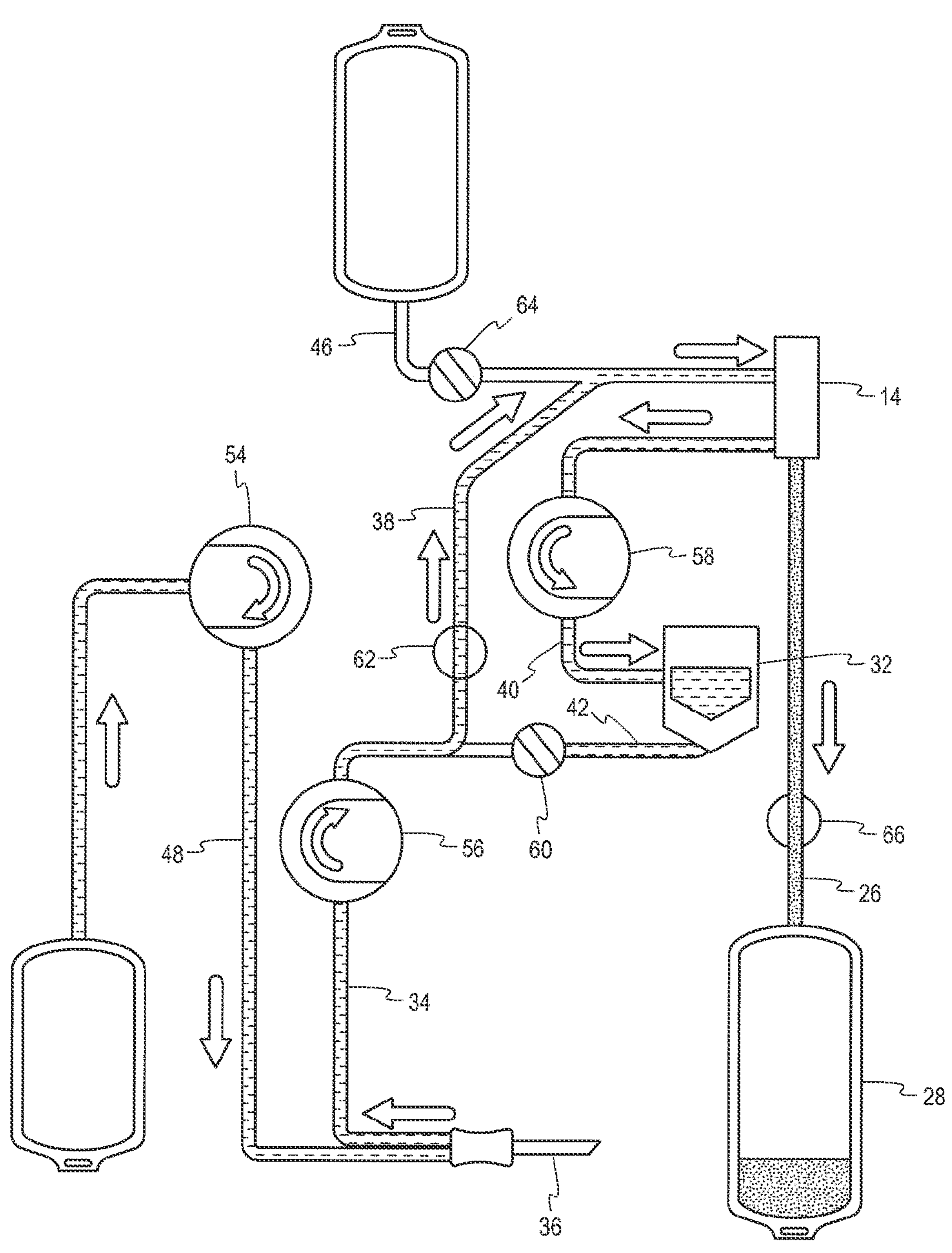
FIG. 4 is a schematic view showing operation of the plasmapheresis system in the collection phase.

The separator 14, best seen in FIG. 2, has a spinning membrane filter 16 mounted to a rotor 18 for rotation within a case 20 to separate blood into components. A detailed description of a spinning membrane separator may be found in U.S. Pat. No. 5,194,145 to Schoendorfer, which is incorporated herein by reference. As can be appreciated, in a different system, separation of the whole blood may be accomplished by centrifugation. See, e.g. U.S. Pat. No. 5,360,542 to Williamson et al.

During plasmapheresis, whole blood is withdrawn from a donor, anticoagulant added, and the anticoagulated whole blood then enters the separator 14 through a whole blood input port 22. The plasma is separated by the spinning membrane filter, and then passes out of a plasma output port 24, through a plasma line 26, and into a plasma collection container 28. Concentrated cells are pumped out of a concentrated cell output port 30 into a reservoir 32, where the cells remain until reinfusion to the donor. As can be appreciated, some of the anticoagulant added to the whole blood will remain with the separated plasma, while another amount of anticoagulant will remain with the concentrated cells.

The disposable set 12 also includes tubing lines for introducing whole blood from the donor into the system during collection and returning concentrated cells to the donor during reinfusion (donor line 34, which terminates in the venipuncture needle 36), and for transporting anticoagulated whole blood to the separator (blood line 38), concentrated cells into the reservoir (cell line 40), concentrated cells from the reservoir to the donor line (reinfusion line 42), plasma into the plasma collection container (plasma line 44), saline (saline line 46), and anticoagulant (AC line 48).

The hardware component 10 includes a programmable controller 50 and touch screen 52 with a graphical user interface ("GUI") through which the operator controls the procedure. For example, the GUI permits entry of any of a donor ID, donor sex, donor height, donor weight, donor age, donor hematocrit/hemoglobin; a target saline infusion volume (if a saline protocol is selected), and a target plasma volume. The touch screen 52 also enables the operator to gather status information and handle error conditions.

Three peristaltic pumps are located on the front panel of the hardware component 10, including an AC pump 54, a blood pump 56, and a cell pump 58. The AC pump 54 delivers anticoagulant solution (AC) at a controlled rate into the blood line 38 as whole blood enters the set from the donor. The blood pump 56 delivers anticoagulated whole blood to the separator during the collection phase of the procedure and returns concentrated cellular components and, if desired, replacement fluid to the donor during the reinfusion phase of the procedure. The cell pump 58 delivers concentrated cellular components from the separator 14 to a reservoir during the collection phase.

The front panel also includes four clamps into which the disposable set 12 is installed, including a reinfusion clamp 60, a blood clamp 62, a saline clamp 64, and a plasma clamp 66. The reinfusion clamp 60 closes to block the reinfusion line (42) during the collection phase (FIG. 5) and is open during the reinfusion phase (FIG. 6) to allow the blood pump to reinfuse the concentrated cellular components from the reservoir 32 to the donor. The blood clamp 62 opens during the collection phase to allow anticoagulated whole blood to be pumped to the separator 14 and closes during the reinfusion phase to block the blood line 38. The saline clamp 64 closes to block the saline line 46 during the collection phase and during reinfusion of the separated cellular components. If saline is to be used as a replacement fluid, the saline clamp 64 opens during the reinfusion phase. The plasma clamp 66 opens during the collection phase to allow plasma to flow into the plasma collection container 28 and closes during the reinfusion phase.

The hardware component 10 includes three weigh scales to monitor the current plasma collection volume (scale 68), the AC solution volume (scale 70), and the concentrated cellular content volume (scale 72). The system also includes various sensors and detectors, including a venous pressure sensor 74, a separator pressure sensor 76, optical blood detectors 78, and an air detector 80.

Figure 5:
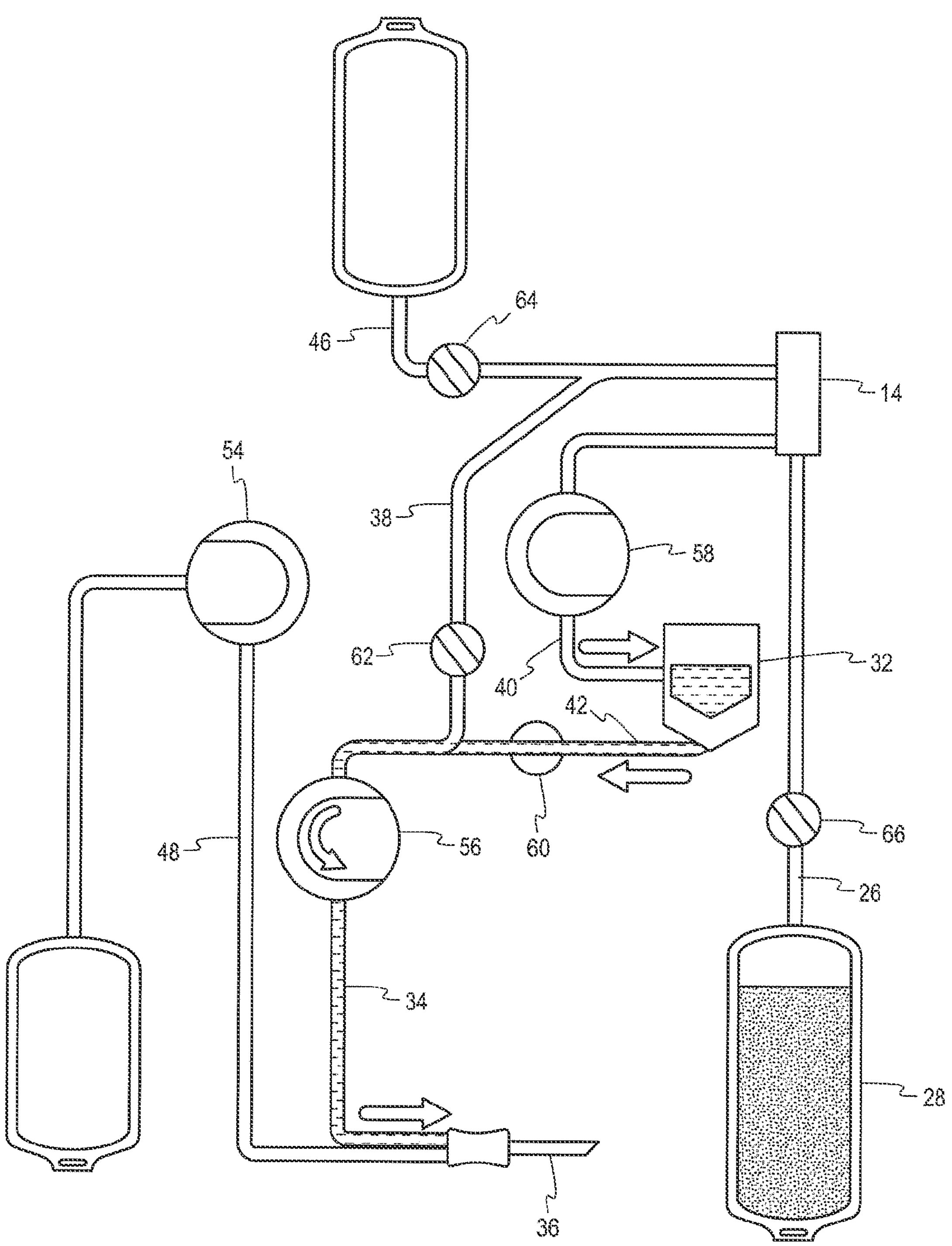
FIG. 5 is a schematic view showing operation of the plasmapheresis system in the reinfusion phase.

The donor is connected to the system throughout the procedure. As illustrated, the disposable set 12 includes a single venipuncture needle 36, through which whole blood is drawn from the donor in a collection phase (FIG. 4) and concentrated cells are returned to the donor in a reinfusion stage (FIG. 5). As noted above, the plasmapheresis procedure may comprise a plurality of cycles each having a collection/separation phase followed by a return or reinfusion phase. During the collection phase, the whole blood is separated into plasma and concentrated cells. The disposable set includes a plasma collection container 28 for receipt of the separated plasma and a reservoir 32 for receipt of the concentrated cells. During the reinfusion phase, the concentrated cells from the reservoir 32 are reinfused to the donor through the venipuncture needle 36. Typically, plasmapheresis performed with a single venipuncture needle 36 involves multiple cycles of collection and reinfusion.

Returning to FIG. 4, during the collection phase, anticoagulant solution (AC) is pumped at a controlled rate and mixed with whole blood as it enters the disposable set 12. The anticoagulated blood is pumped to the separator 14, where plasma is separated from the cellular components and directed to the plasma collection container 28.

The cellular components are pumped from the separator 14 to the reservoir 32. The collection phase stops when the reservoir 32 reaches an expected volume of concentrated cells or if the target plasma collection volume has been achieved.

Then, the reinfusion phase begins. With reference to FIG. 5, during the reinfusion phase, the blood pump 56 reverses direction and pumps the concentrated cells from the reservoir 32 back to the donor through the apheresis needle 36. If a saline protocol was selected, by which saline is returned to the donor as a replacement fluid for the collected plasma, the final reinfusion phase is followed by saline infusion.

In keeping with the application, an estimate of the volume of anticoagulant that will be required for the procedure is determined, so that a single container of anticoagulant may be connected to the disposable set 14 prior to commencement of the procedure. To this end, the donor's total blood volume (TBV) and the amount of plasma that may be collected from the donor are determined using donor-specific characteristics. Various nomograms may be adopted for this purpose.

The donor-specific characteristics used comprise at least the donor's weight and a hematocrit, as the hematocrit is needed to determine the percentage of anticoagulant that is collected along with the plasma in the plasma product container. The hematocrit may be a default value, such as a "worst-case" scenario in which the donor's hematocrit is assumed to be 54%, or the hematocrit of the donor may be determined using any number of well-known methods, such as by use of a dedicated hematocrit centrifuge (e.g., the SciLogex DM4124 Hematocrit Centrifuge) or hematology analyzer (e.g., the Sysmex XP-300™ Automated Hematology Analyzer.

The donor hematocrit can also vary during the plasmapheresis procedure as a function of the amount of plasma collected. More specifically, because the donor loses plasma as the procedure progresses, the donor's hematocrit will be higher in a later part of the procedure. Accordingly, more anticoagulant will be required that that indicated in the initial estimate based on the donor's initial hematocrit. Thus, the estimate of anticoagulant based on the donor's initial hematocrit may be increased to account for the increasing hematocrit.

By way of example, if the donor's total blood volume is determined to be 5000 mL, and the donor's hematocrit at the beginning of the procedure is 40%, red blood cells will constitute 2000 mL and plasma 3000 mL. After 500 mL of plasma has been collected and the associated red blood cells reinfused to the donor, the donor will have a total blood volume of 4500 mL, with 2000 mL of red blood cells and 2500 mL of plasma, for a hematocrit of 44.4% (2000 mL/(2000 mL+2500 mL), or an increase in hematocrit of 4.4%. The increase in hematocrit will be a function of the size of the donor (for larger donors having a larger total blood volume and, consequently, a larger total plasma volume, the change in hematocrit will be less), and how much plasma has been collected. Due to the increase in hematocrit, the amount of anticoagulant required for subsequent plasma collection will increase. Thus, based on the targeted plasma collection volume, a "final' hematocrit of the donor can be estimated, which will be higher than the initial hematocrit. A hematocrit for the entire procedure may be based on an average between the initial and final hematocrits of the donor, and the average value used when determining the total amount of anticoagulant that will be required for the plasma collection procedure. The amount of anticoagulant that is returned to the donor along with the red blood cells, which would also lower the hematocrit of the donor, may also be taken into account in determining the average hematocrit over the course of the procedure.

The donor-specific characteristics may be entered into the controller by the operator using the touch screen. Alternatively, the donor-specific characteristics may be provided to the controller through a data management system that includes a data base including such information.

When the donor's weight and a hematocrit value are the only donor-specific characteristics used, a three-tier nomogram, such as the FDA nomogram described above, can be adopted, in which three different weight classes of donors are utilized (between 110 lbs. and 149 lbs., between 150 lbs. and 174 lbs., and 175 lbs. and up). For example, under the FDA nomogram, if the donor weighs 180 lb., 800 mL of plasma and 880 mL of plasma product (plasma plus anticoagulant) may be collected. The volume of anticoagulant in the plasma product may then be calculated using hematocrit, either default or donor-specific.

Alternatively, a donor's total blood volume may be determined using the donor's weight and height, by using, for example the Lemmens formula, in which the total blood volume is based on the BMI (Body Mass Index) of the donor ($TBV=70/\sqrt{(BMI/22)}$). Then the donor's hematocrit is applied to the donor's total blood volume to determine the total plasma volume (TPV), with a certain percentage of the TPV being established as the target volume of plasma to be collected from the donor, with an upper limit established (such as 1000 mL).

In a further alternative, a donor's total blood volume may be determined using the donor's weight, height, and gender, by using, for example, the Nadler equations, with the donor's hematocrit then being applied as described above to determine the total plasma volume of the donor and the target volume of plasma to be collected.

As can be appreciated, the methodologies for determining total blood volume described above are exemplary. Any other generally accepted methodology for determining donor's total blood volume may also be used, such as any of those described in US 2020/0147289, which is incorporated herein by reference.

Once either of the target volume of plasma to be collected or the target volume for the plasma product (plasma plus anticoagulant) is determined, the percentage of anticoagulant that will comprise the plasma product can be determined by applying the donor hematocrit. For example, the percentage of anticoagulant is equal to 1/(1+ACR*(1−HCT/100)).

Once the volume and/or percentage of anticoagulant to be collected with the plasma is calculated, the amount of anticoagulant that will be returned/reinfused to the donor along with the concentrated cells can be determined based on the efficiency of the blood separator. The efficiency of a separator is defined as the ratio of the liquid portion that is output from the separator to the liquid porting that is input to the separator. For example, if 100 mL of anticoagulated whole blood having a hematocrit of 40% is to be separated, 60 mL comprises liquid (primarily plasma plus anticoagulant) and 40 mL comprises cellular material (primarily red blood cells), and if 40 mL of liquid is collected after separating the anticoagulated whole blood, the separator has an efficiency of 40/60=67%. If the blood separator has an efficiency of 67%, then 67% of the anticoagulant is retained with the plasma that is collected, and 33% of the anticoagulant is being reinfused in the donor along with the concentrated cells.

Separation efficiency is a function of multiple parameters, and different parameters are implicated depending on the technology. For example, hematocrit has a strong influence on the efficiency of centrifugal separators. (See, e.g., R. I. Brown, The Physics of Continuous Flow Centrifugal Cell Separation, Artificial Organs 13(1): 4-20 (1989)). The anticoagulant ratio also has an effect on separation efficiency, as the higher the anticoagulant ratio, the lower the hematocrit of the anticoagulated whole blood that is to be separated, and lower hematocrit blood will separate with higher efficiency. For spinning membrane separation technologies, the surface area of the membrane has a greater effect than hematocrit. (See, e.g., U.S. Pat. Nos. 8,840,790 and 10,046,278). In general, the separation efficiency is determined beforehand and either input to the controller by the operator or is pre-programmed into the controller.

In addition, the determination of the volume of anticoagulant that will be needed may also take into account anticoagulant that is commonly introduced into the disposable kit prior to the commencement of the plasmapheresis procedure in pre-processing steps, such as for priming the disposable kit, performing one or more pre-cycles, or for performing other pre-procedure steps. Such pre-procedure volumes of anticoagulant may vary depending on the disposable kit. They are typically determined empirically and may be pre-programmed into the system controller or input by the operator.

The volume of anticoagulant that will be needed may also be increased by a predetermined volume, such as by from 25 mL to 50 mL, to provide for a margin of safety so that the container of anticoagulant will not empty before the completion of the plasmapheresis procedure.

As can be appreciated, many of the steps that are performed in arriving at a predicted total volume of anticoagulant, may be pre-programmed into the controller of the system so that they can be performed automatically upon appropriate input by the operator of the relevant donor-specific characteristics.

Once a predicted value for the total volume of anticoagulant that will be required for the procedure is determined, a single container of anticoagulant having at least the predicted total volume is connected to the disposable kit. In practice, anticoagulant is provided in containers containing from 250 mL of anticoagulant to 1000 mL of anticoagulant. Thus, the single container of anticoagulant that is attached to the disposable set contains 250 mL of anticoagulant, if the total volume of anticoagulant that is predicted to be required for the procedure ($V_{ACT}$) is <250 mL; 500 ml of anticoagulant, if 250 mL<VACT<500 mL; 750 mL of anticoagulant, if 500 mL<VACT<750 mL; and 1000 mL of anticoagulant, if 750 mL<VACT<1000 mL. The volume of the container of anticoagulant to be attached can be presented to the operator in the form of a recommendation that is viewable on a display associated with the controller. Additionally, $V_{ACT}$ may be compared to an inventory of containers of anticoagulant and, if $V_{ACT}$ is greater than a volume of anticoagulant in the inventory, a further notice may be provided to the operator so that additional containers of anticoagulant can be obtained before starting the procedure.

Figure 6:
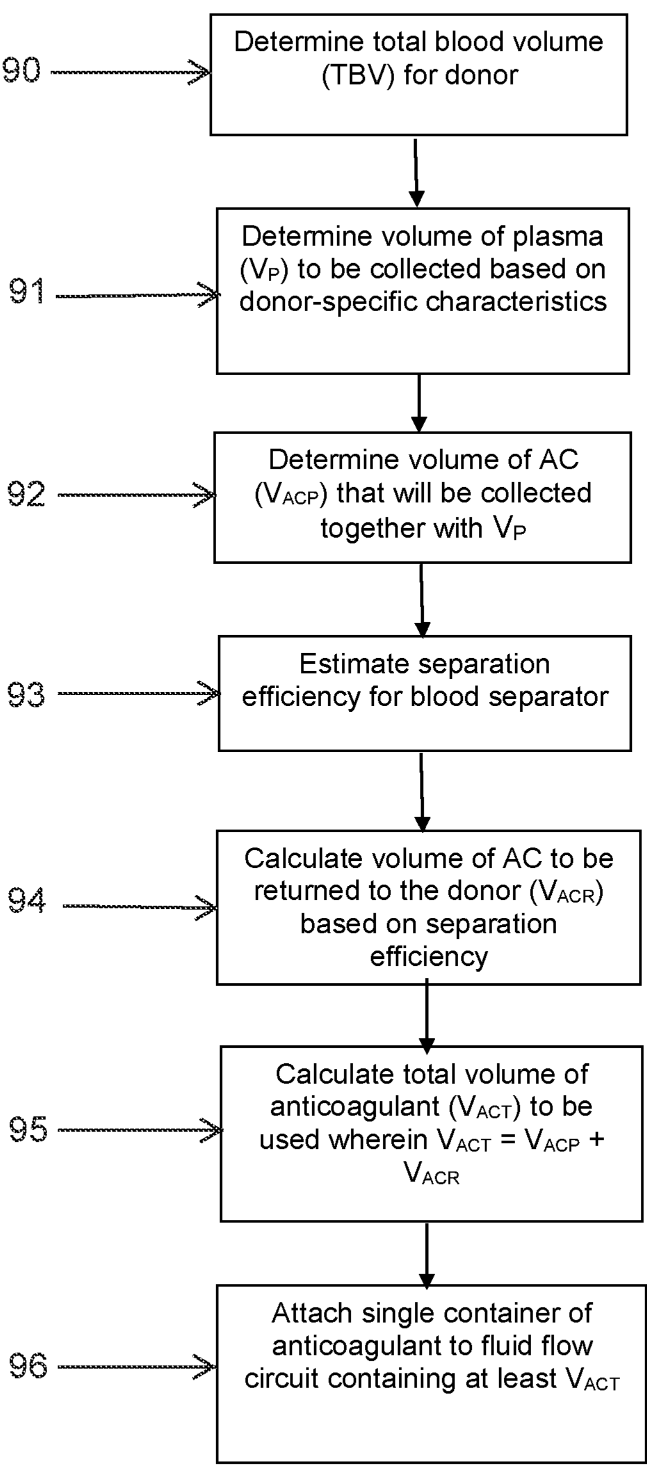
FIG. 6 is a flow chart illustrating the steps of a method in accordance with the present application.

The basic steps of the method are illustrated by way of the flow chart comprising FIG. 6 of this application. With reference to FIG. 6, the method comprises a first step of determining a total blood volume (TBV) for a donor (Box 90); a second step of determining a volume of plasma (VP) to be collected from the donor based on donor-specific characteristics (Box 91); a third step of determining a volume of anticoagulant ($V_{ACP}$) that will be collected together with the volume of plasma VP (Box 92); a fourth step of estimating a separation efficiency for the blood separator (Box 93); a fifth step of calculating a volume of anticoagulant to be returned to the donor ($V_{ACR}$) based on the separation efficiency (Box 94); a sixth step of calculating a total volume of anticoagulant ($V_{ACT}$) to be used wherein VACT=VACP+VACR (Box 95); and a seventh step of attaching a single container of anticoagulant to the fluid flow circuit containing at least $V_{ACT}$ (Box 96), with each of steps illustrated in Boxes 90-96 being performed prior to connecting the donor to the fluid flow circuit. As can be appreciated once the donor-specific characteristics are entered into the controller, either by the operator or a data management system, the controller can automatically perform steps 90-92, 94 and 95, and make a recommendation as to the volume of the container of anticoagulant that is to be attached to the disposable kit.

It will be understood that the embodiments described are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope of the claims is not limited to the above-description, but is set forth in the following claims.

What is claimed is:

1. A method for performing plasmapheresis using a fluid flow circuit and a blood separator, comprising:

a) determining a total blood volume (TBV) for a donor;

b) determining a volume of plasma ($V_P$) to be collected from the donor based on donor-specific characteristics;

c) determining a volume of anticoagulant ($V_{ACP}$) that will be collected together with the volume of plasma $V_P$;

d) calculating a volume of anticoagulant to be returned to the donor ($V_{ACR}$) based on a separation efficiency for the blood separator;

e) calculating a total volume of anticoagulant ($V_{ACT}$) to be used; and f) preparing one or more containers of anticoagulant for attachment to the fluid flow circuit containing in total at least $V_{ACT}$, or attaching a single container of anticoagulant to the fluid flow circuit containing at least $V_{ACT}$;

g) wherein steps a)-g) are performed prior to connecting the donor to the fluid flow circuit.

2. The method of claim 1, wherein the donor-specific characteristics comprise weight and hematocrit.

3. The method of claim 2, wherein the hematocrit is a default value.

4. The method of claim 3, wherein the default value for the hematocrit is representative of a worst-case scenario.

5. The method of claim 4, wherein the default value for the hematocrit is 54%.

6. The method of claim 2, wherein the hematocrit of the donor is measured.

7. The method of claim 1, wherein the donor-specific characteristics comprise weight, height, and hematocrit.

8. The method of claim 1, wherein the donor-specific variables comprise weight, height, gender, and hematocrit.

9. The method of claim 1 wherein the one or more containers or the single container contain 250 ml of anticoagulant, if $V_{ACT}$<250 mL; 500 ml of anticoagulant, if 250 mL<$V_{ACT}$<500 mL; 750 ml of anticoagulant, if 500 mL<$V_{ACT}$<750 ML; and 1000 mL of anticoagulant, if 750 mL<$V_{ACT}$<1000 mL.

10. The method of claim 1, wherein $V_{ACP}=V_P/(1+ACR^*(1-Hct/100))$; wherein ACR is a ratio of anticoagulant to whole blood and Het is a hematocrit of the donor.

11. The method of claim 1 wherein a separation efficiency for the blood separator is determined based, at least in part, on a hematocrit of the donor.

12. The method of claim 1 wherein the separation efficiency for the blood separator is based, at least in part, on a ratio of anticoagulant to whole blood (ACR) to be used.

13. The method of claim 1 wherein $V_{ACT}=V_{ACP}+V_{ACR}$.

14. The method of claim 11 wherein $V_{ACT}$ is determined based on an estimated volume of whole blood to be processed to reach the volume of plasma to be collected, $V_P$, and the separation efficiency.

15. The method of claim 1 wherein $V_{ACT}$ additionally includes a volume of anticoagulant to be used for priming the fluid flow circuit and blood separator.

16. The method of claim 1 wherein $V_{ACT}$ is increased to provide a margin of safety.

17. The method of claim 15, wherein $V_{ACT}$ is increased to provide a margin of safety.

18. The method of claim 17, wherein $V_{ACT}$ is increased by from 25 mL to 50 mL.

19. The method of claim 1 further comprising comparing $V_{ACT}$ to an inventory of containers of anticoagulant and, determining whether $V_{ACT}$ is greater than a volume of anticoagulant in the inventory.

20. An automated system for separating plasma from whole blood comprising a disposable fluid flow circuit including a separator for separating whole blood into a plasma fraction and a concentrated cell fraction and a reusable hardware component comprising a programmable controller having a touch screen for receiving input from an operator and configured to provide, based on operator input, a calculation of a total volume of anticoagulant needed for a procedure and, wherein the programmable controller is configured to calculate:

a total blood volume (TBV) for a donor;

a volume of plasma ($V_P$) to be collected from the donor based on donor-specific characteristics;

a volume of anticoagulant ($V_{ACP}$) that will be collected together with the volume of plasma $V_P$;

a volume of anticoagulant to be returned to the donor ($V_{ACR}$) based on an estimated separation efficiency for the separator;

a total volume of anticoagulant ($V_{ACT}$) to be used; and to display $V_{ACT}$ on the touch screen.

21. The automated system of claim 20 wherein the programmable controller is further configured to make a recommendation as to a total volume of anticoagulant to be attached to the disposable fluid flow circuit based on $V_{ACT}$, wherein the recommendation is that either a single container or multiple containers are provided that contain 250 ml of anticoagulant, if $V_{ACT}$<250 ml; 500 ml of anticoagulant, if 250 mL<$V_{ACT}$<500 ML; 750 ml of anticoagulant, if 500 mL<$V_{ACT}$<750 mL; and 1000 mL of anticoagulant, if 750 mL<$V_{ACT}$<1000 mL.

* * * * *